United States Patent
Reed et al.

(10) Patent No.: US 8,181,528 B2
(45) Date of Patent: May 22, 2012

(54) METHOD AND SYSTEM FOR ULTRASONIC INSPECTION OF GEARBOX RING GEAR

(75) Inventors: Francis A. Reed, Princetown, NY (US);
John T. Murphy, Niskayuna, NY (US);
George R. Silliman, Rensselaer, NY (US)

(73) Assignee: General Electric Company, Schenectady, NY (US)

( * ) Notice: Subject to any disclaimer, the term of this patent is extended or adjusted under 35 U.S.C. 154(b) by 439 days.

(21) Appl. No.: 12/394,160

(22) Filed: Feb. 27, 2009

(65) Prior Publication Data

US 2010/0218609 A1  Sep. 2, 2010

(51) Int. Cl.
*G01N 29/07* (2006.01)

(52) U.S. Cl. .............................. 73/598; 73/597; 73/596
(58) Field of Classification Search ...................... 73/598
See application file for complete search history.

(56) References Cited

U.S. PATENT DOCUMENTS

| | | | |
|---|---|---|---|
| 5,963,882 A | 10/1999 | Viertl et al. | |
| 6,725,722 B1 | 4/2004 | Murphy et al. | |
| 6,807,860 B1 | 10/2004 | Reed et al. | |
| 6,857,330 B2 | 2/2005 | Murphy et al. | |
| 6,952,967 B2 * | 10/2005 | Koo et al. | 73/632 |
| 7,010,982 B2 | 3/2006 | Bergman | |
| 7,017,414 B2 | 3/2006 | Falsetti et al. | |
| 7,086,285 B2 | 8/2006 | Reed | |
| 7,093,491 B2 | 8/2006 | Murphy et al. | |
| 7,275,442 B2 | 10/2007 | Bentzel | |
| 7,389,693 B2 | 6/2008 | Reed et al. | |
| 7,426,865 B2 | 9/2008 | Reed | |
| 2007/0058854 A1 * | 3/2007 | Caskey et al. | 382/152 |
| 2008/0141778 A1 * | 6/2008 | Bosselmann et al. | 73/633 |

* cited by examiner

*Primary Examiner* — Hezron E Williams
*Assistant Examiner* — Gregory J Redmann
(74) *Attorney, Agent, or Firm* — James W. Pemrick; Ernest G. Cusick; Frank A. Landgraff

(57) ABSTRACT

A method and system for ultrasonically inspecting a ring gear of a gearbox is provided. The method and system can be used for the detection, characterization and/or sizing of defects in the ring gear. The ring gear has a plurality of teeth, which extend radially inward with respect to an outer surface of the gearbox. The method includes the steps of selecting an ultrasonic transducer productive of a test signal, positioning the ultrasonic transducer at an outer surface of the ring gear, orienting the ultrasonic transducer so as to direct the test signal to propagate through the ring gear, and activating the ultrasonic transducer so as to test the ring gear for defects therein.

14 Claims, 4 Drawing Sheets

METHOD AND SYSTEM FOR ULTRASONIC INSPECTION OF GEARBOX RING GEAR

BACKGROUND OF THE INVENTION

The present disclosure relates generally to a method for inspecting the ring gear in a gearbox, and particularly to a method for inspecting a ring gear in a gearbox for the detection, characterization and/or sizing of defects therein.

Recently, wind turbines have received increased attention as environmentally safe and relatively inexpensive alternative energy sources. With this growing interest, considerable efforts have been made to develop wind turbines that are reliable and efficient.

Generally, a wind turbine includes a rotor having multiple blades. The rotor is mounted to a housing or nacelle, which is positioned on top of a truss or tubular tower. Utility grade wind turbines (i.e., wind turbines designed to provide electrical power to a utility grid) can have large rotors (e.g., 30 or more meters in diameter). Blades on these rotors transform wind energy into a rotational torque or force that drives one or more generators that may be rotationally coupled to the rotor through a gearbox. The gearbox steps up the inherently low rotational speed of the turbine rotor for the generator to efficiently convert mechanical energy to electrical energy, which is typically fed into a utility grid.

Wind turbine gearboxes are subject to a large amount of loads. Most of these loads are from the rotor and can include main shaft torque, weight of the rotor, axial thrust forces and other dynamic loads. Some of these loads will be steady, some may be transient, while others may vary randomly or periodically. All of the loads contribute to fatigue damage and wear on the various components of the gearbox. Because the gearbox is difficult to remove and replace, failure of any gearbox component can result in a lengthy and expensive repair process. For example, to remove a gearbox from an existing wind turbine, a large crane must be transported to and erected on site. The wind turbine will be off-line and out of energy production during the repair process.

One component of a gearbox that can fail is the ring gear. One known inspection method for the ring gear is a visual inspection using borescope-type equipment. Visual testing can be used to find large defects such as missing sections of the gear teeth but the capability of the inspection for finding small crack-like defects is not as high as possible. Improving the capability of the visual inspection would result in a time-consuming evaluation resulting in increased downtime and expense. Any inspection method which uses the borescope holes in the gearcase for access will have limited capability for finding small crack-like defects. For instance, any visual surface inspection method would need to interrogate each gear tooth surface. This process would be very difficult, if possible, due to the limited amount of access ports.

BRIEF DESCRIPTION OF THE INVENTION

In one aspect of the present invention, a method for ultrasonically inspecting a ring gear of a gearbox is provided. The method can be used for the detection, characterization and/or sizing of defects in the ring gear. The ring gear has a plurality of teeth, which extend radially inward with respect to an outer surface of the gearbox. The method includes the steps of selecting an ultrasonic transducer productive of a test signal, positioning the ultrasonic transducer at an outer surface of the ring gear, orienting the ultrasonic transducer so as to direct the test signal to propagate through the ring gear, and activating the ultrasonic transducer so as to test the ring gear for defects.

In another aspect of the present invention, a method for inspecting a component of a wind turbine is provided. The method can be used for the detection, characterization and/or sizing of defects in the component. The component has a plurality of teeth, which extend radially inward with respect to an outer surface of the component. The method includes the steps of selecting a transducer productive of a test signal, positioning the transducer at an outer surface of the component, orienting the transducer so as to direct the test signal to propagate through at least a portion of the component, and activating the transducer so as to test the component for defects.

In yet another aspect of the present invention, a system for inspecting a component of a wind turbine is provided. The system can be used for the detection, characterization and/or sizing of defects in the component. The component has a plurality of teeth extending radially inward with respect to an outer surface of the component. The system includes a transducer productive of a test signal, and the transducer is positioned at an outer surface of the component. The transducer is oriented so as to direct the test signal to propagate through at least a portion of the component, and is employed to test the component for defects.

BRIEF DESCRIPTION OF THE DRAWINGS

Referring to the exemplary drawings wherein like elements are numbered alike in the accompanying Figures.

DETAILED DESCRIPTION OF THE INVENTION

Figure 1:
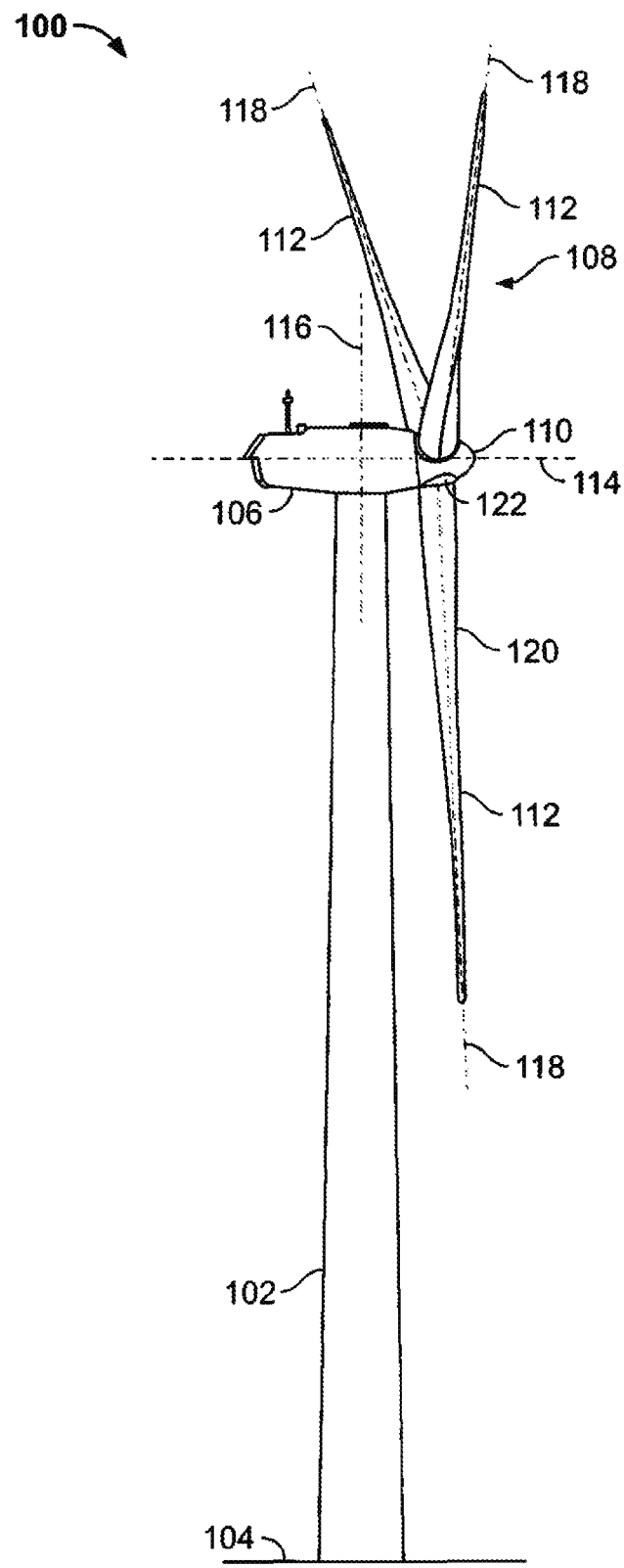
FIG. 1 is a schematic illustration of an exemplary wind turbine generator.

FIG. 1 is a schematic illustration of an exemplary wind turbine 100. In the exemplary embodiment, wind turbine 100 is a horizontal axis wind turbine. Alternatively, wind turbine 100 may be a vertical axis wind turbine. Wind turbine 100 has a tower 102 extending from a supporting surface 104, a nacelle 106 mounted on tower 102, and a rotor 108 coupled to nacelle 106. Rotor 108 has a rotatable hub 110 and a plurality of rotor blades 112 coupled to hub 110. In the exemplary embodiment, rotor 108 has three rotor blades 112. In an alternative embodiment, rotor 108 may have more or less than three rotor blades 112. In the exemplary embodiment, tower 102 is fabricated from tubular steel and has a cavity (not shown in FIG. 1) extending between supporting surface 104 and nacelle 106. In an alternate embodiment, tower 102 is a lattice tower. The height of tower 102 is selected based upon factors and conditions known in the art.

Blades 112 are positioned about rotor hub 110 to facilitate rotating rotor 108 to transfer kinetic energy from the wind into usable mechanical energy, and subsequently, into electrical energy. Blades 112 are mated to hub 110 by coupling a blade root portion 120 to hub 110 at a plurality of load transfer regions 122. Load transfer regions 122 have a hub load transfer region and a blade load transfer region (both not shown in FIG. 1). Loads induced in blades 112 are transferred to hub 110 via load transfer regions 122.

In the exemplary embodiment, blades 112 have a length between about 50 meters (m) (164 feet (ft)) and about 100 m (328 ft). Alternatively, blades 112 may have any length. As the wind strikes blades 112, rotor 108 is rotated about rotation axis 114. As blades 112 are rotated and subjected to centrifugal forces, blades 112 are subjected to various bending moments and other operational stresses. As such, blades 112 may deflect and/or rotate from a neutral, or non-deflected, position to a deflected position and associated stresses, or loads, may be induced in blades 112. Moreover, a pitch angle of blades 112, i.e., the angle that determines blades 112 perspective with respect to the direction of the wind, may be changed by a pitch adjustment mechanism (not shown in FIG. 1) to facilitate increasing or decreasing blade 112 speed by adjusting the surface area of blades 112 exposed to the wind force vectors. Pitch axes 118 for blades 112 are illustrated. In the exemplary embodiment, the pitches of blades 112 are controlled individually. Alternatively, the pitches of blades 112 may be controlled as a group.

In some configurations, one or more microcontrollers in a control system (not shown in FIG. 1) are used for overall system monitoring and control including pitch and rotor speed regulation, yaw drive and yaw brake application, and fault monitoring. Alternatively, distributed or centralized control architectures are used in alternate embodiments of wind turbine 100.

Figure 2:
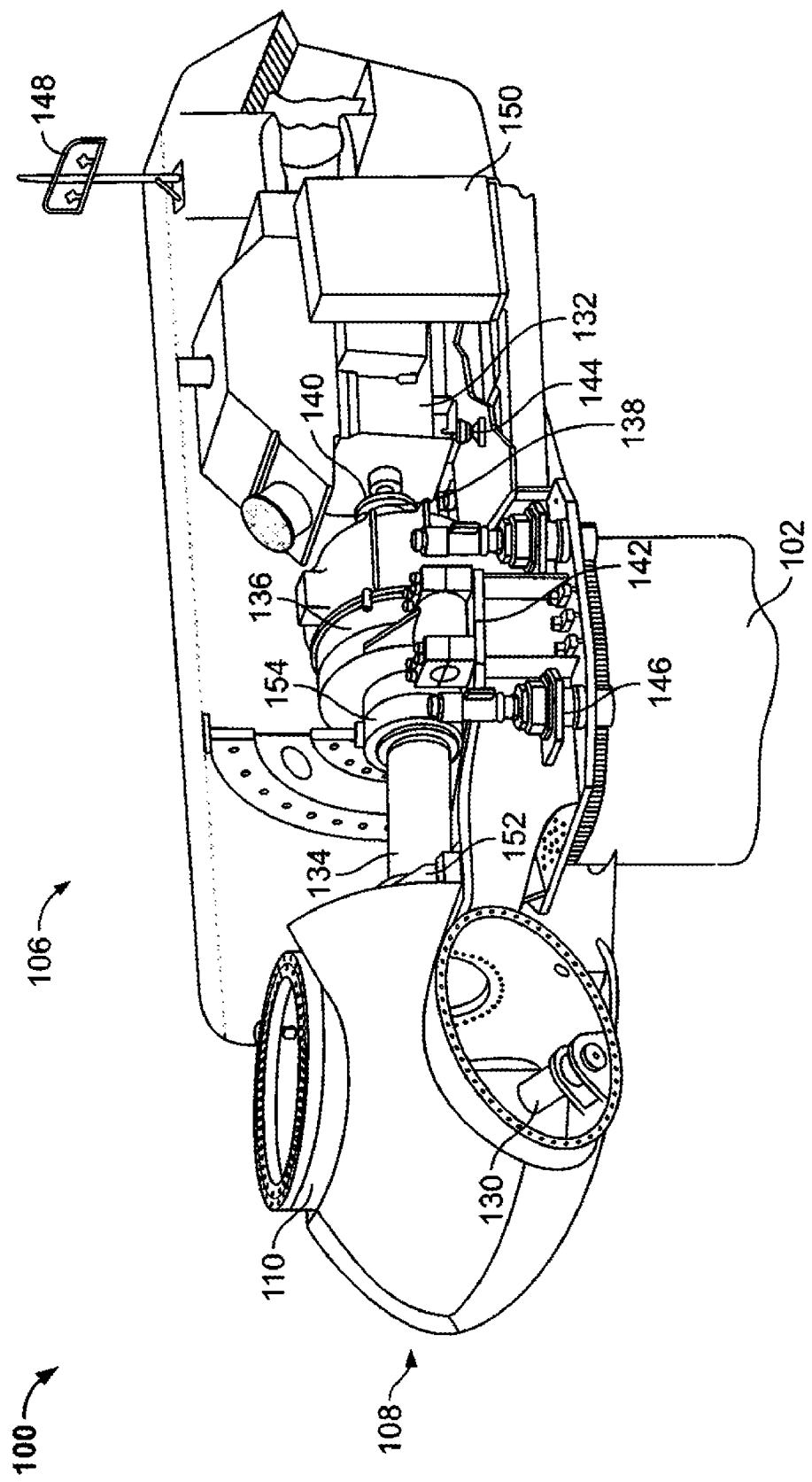
FIG. 2 is a fragmentary cross-sectional schematic illustration of a nacelle that may be used with the exemplary wind turbine generator shown in FIG. 1.

FIG. 2 is a fragmentary cross-sectional schematic view of nacelle 106 of exemplary wind turbine 100. Various components of wind turbine 100 are housed in nacelle 106 atop tower 102 of wind turbine 100. Pitch drive mechanisms 130 (only one illustrated in FIG. 2) modulate the pitch of blades 112 along pitch axis 118 (both shown in FIG. 1).

Rotor 108 is rotatably coupled to an electric generator 132 positioned within nacelle 106 via rotor shaft 134, sometimes referred to as low speed shaft 134, a gearbox 136, a high speed shaft 138, and a coupling 140. Forward and aft support bearings 152 and 154, respectively, facilitate radial support and alignment of shaft 134. Some wind turbines may omit the forward or aft support bearings, or have bearings integrated within the gearbox. Rotation of shaft 134 rotatably drives gearbox 136 that subsequently rotatably drives shaft 138. Typically, a lubricating oil is used within gearbox 136. Shaft 138 rotatably drives generator 132 via coupling 140 and shaft 138 rotation facilitates generator 132 production of electrical power. Gearbox 136 and generator 132 are supported by supports 142 and 144, respectively.

Also positioned in nacelle 106 is a yaw adjustment mechanism 146 that may be used to rotate nacelle 106 and rotor 108 on axis 116 (shown in FIG. 1) to control the perspective of blades 112 with respect to the direction of the wind. Mechanism 146 is coupled to nacelle 106. Meteorological mast 148 includes a wind vane and anemometer (neither shown in FIG. 2). Mast 148 is positioned on nacelle 106 and provides information to the turbine control system that may include wind direction and/or wind speed. In alternative embodiments, mast 148 can be mounted on hub 110 and extend in a direction in front of rotor 108.

A portion of the turbine control system resides within control panel 150. The turbine control system (TCS) controls and monitors various systems and components of wind turbine 100. A plurality of sensors are distributed throughout wind turbine 100 and the status of various conditions (e.g., vibration level, temperature, etc.) are monitored. The sensed conditions are utilized by the TCS to control various subsystems of wind turbine 100.

Gearboxes in wind turbines are large components and require great effort and expense to remove and repair. It would be highly beneficial to detect flaws at an early stage to properly schedule gearbox repair and/or replacement. One such flaw can occur in the ring gear of the gearbox. A ring gear failure or defect (e.g., a cracked or missing gear tooth) can result in the shutdown of the wind turbine requiring repair and/or replacement of the gearbox.

According to aspects of the present invention, a method is provided for nondestructively inspecting ring gears that uses ultrasonic waves transmitted from the outer diameter of the ring gear. The ultrasonic waves can be used to evaluate the volume of the ring gear and the gear teeth located on the inner diameter. The method can use a combination of beam angles to interrogate the ring gear. The method may use fixed-angle monolithic ultrasonic probes and/or one or more phased-array probes operating at multiple angles generating a sector scan. The method can detect and identify defects in the volume of the ring gear including defects in the gear teeth.

One primary area of interest for on-site inspection of wind turbine gearboxes is the evaluation of the ring gear teeth. Aspects of the present invention can incorporate a damage tolerance design methodology, which can help detect small flaws in the gear teeth. If cracks can be detected at an early stage, before serious damage has occurred, then a scheduled outage can be planned to minimize down-time, expense and loss of energy production.

The method, according to aspects of the present invention, is an inspection method performed from the outer diameter of the ring gear. The inspection method can use ultrasonic inspection technology where one or more ultrasonic transducers are situated on the outer diameter of the ring gear. On many wind turbine gearboxes, the outer diameter of the ring gear is one of the outer surfaces of the gearbox. This surface can be easily accessed for inspection of the ring gear.

The ultrasonic inspection method can include ultrasonic scans performed at one or several beam angles. The angles can be chosen to optimize the detection of crack-like defects located in the gear teeth or volume of the ring gear. Other angles can be chosen to optimize detection of flaws generated from the manufacturing process, flaws initiated during service use, or any other desired flaw of interest.

The ultrasonic transducer may be either a monolithic (single-crystal) operated at a 0-degree beam angle or mounted to a wedge to generate ultrasonic beams at angles other than 0 degrees. A phased-array transducer may also be used to generate a range of beam angles or multiple beam angles used for the ring gear evaluation. Other transducers could also be used, such as an electromagnetic acoustic transducer (EMAT), piezoelectric transducer, or monolithic piezoelectric transducer (MPT). A piezoelectric transducer may be comprised of a monolithic device or an array of separate elements. The transducer may be of the pulse-echo type, where one transducer produces and transmits the signal and the same transducer receives the reflected signal for subsequent analysis. However, the method may use a "pitch-catch" diagnostic technique, where at least one transmitting device transmits a signal and at least one receiving device receives the signal. The pitch-catch mode can include a single device that transmits and receives, or multiple devices where one or more transmitting devices and one or more receiving devices are used. The transmitting and receiving devices may be embodied in one assembly such as a "dual-element" transducer configuration.

Multiple beam angles can be used to optimize detection of flaws or to provide complete coverage of the volume of the ring gear. Some ring gears such as those used in wind turbine gearboxes have machined holes in the volume of the gear. Scanning the transducer using several beam angles will allow complete evaluation of the volume of the ring gear.

The ultrasonic transducer, according to one aspect of the present invention, can be scanned on the outside diameter of the ring gear. The transducer generates ultrasonic wave packets that are transmitted into the ring gear. The wave packets propagate through the ring gear material. If flaws are present in the ring gear, the sound will reflect from the flaws. The reflected sound waves propagating from the flaws will either follow a direct path back to the transducer or propagate to a surface of the ring gear where they will reflect and propagate towards the transducer. The transducer will then receive the reflected ultrasonic waves and convert the acoustic energy into electrical energy. The electrical signals will then be analyzed using ultrasonic test equipment to measure the time-of-flight for the wave reflections, the amplitude of the reflected signals, and other characteristics of the reflections such as phase, frequency, and waveform shape. This information along with the transducer beam angle and location of the transducer on the periphery of the ring gear can be used to determine the size and location of the defect or flaw in the ring gear.

One advantage to the method of the present invention is that there is no requirement to open the borescope holes for access, as required by the known prior art inspection methods. This test is also performed from the outside surfaces of the gearbox, where access is facilitated. The evaluation of the full ring gear can be performed quickly with the ultrasonic inspection method according to the present invention, and is faster than the known visual inspection methods, which require visually reviewing all gear tooth surfaces for small flaws.

Figure 3:
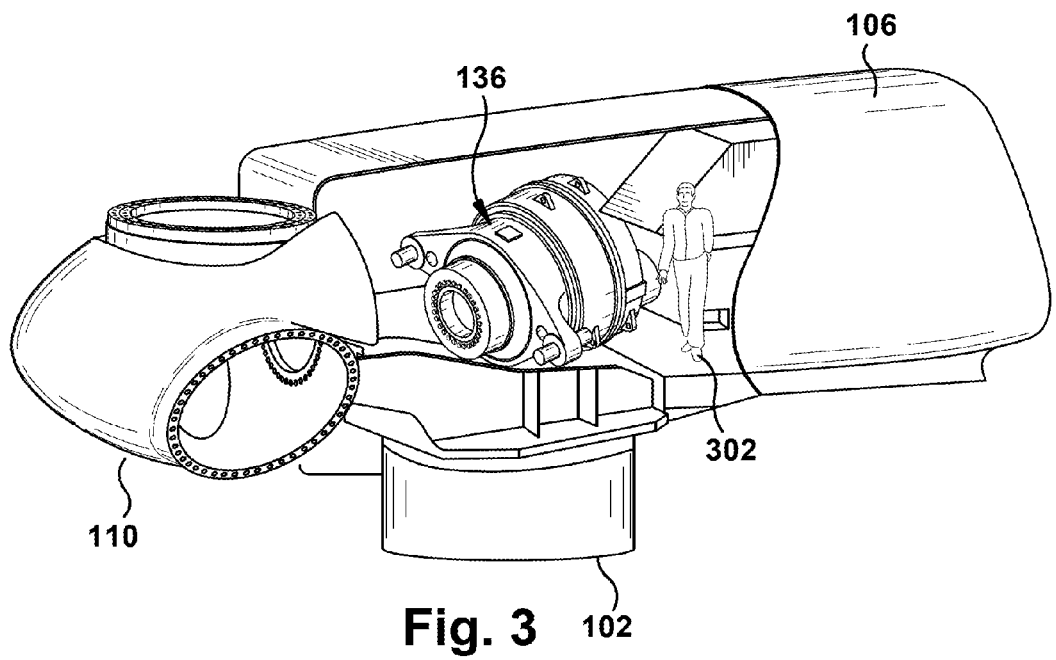
FIG. 3 is a simplified, cut-away illustration of a wind turbine that includes a gearbox.

FIG. 3 illustrates a simplified view of gearbox 136 in accordance with one embodiment of the invention. The silhouette 302 of the person standing inside the wind turbine housing indicates the approximate size of the gearbox 136 in comparison to service personnel. However, gearbox 136 can be of a variety of sizes, shapes, types and configurations. As can be seen, service personnel have good access around the entire outer casing of gearbox 136.

Figure 4:
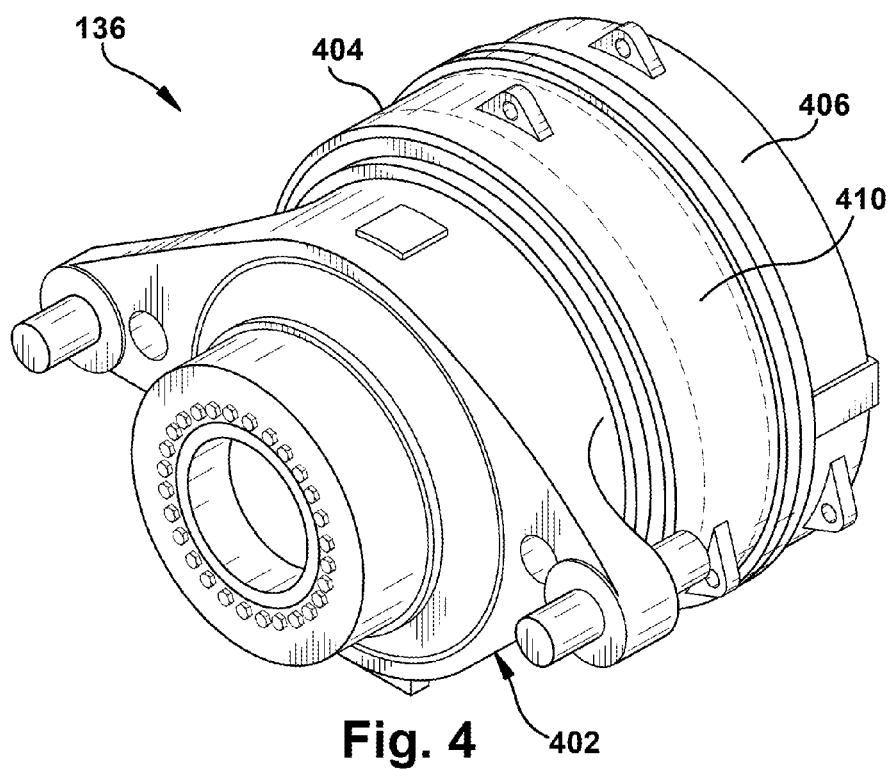
FIG. 4 is a perspective illustration of the input end of the gearbox of Figure.

FIG. 4 illustrates an enlarged perspective view of the gearbox 136. The gearbox 136 includes a gearbox housing that as illustrated is made of several components or covers that are detachably secured together. The gearbox housing, as illustrated, includes an input end cover 402, a ring gear 404, and a final stage cover 406. The ring gear teeth (not shown) extend along the interior surface of ring gear 404 as shown by the area 410 between the dotted lines as illustrated in FIG. 4. In many gearboxes, the ring gear is assembled to the gearbox without a ring gear cover, and the external surfaces of the ring gear form part of the outside of the gearbox. As described previously, the ring gear has been difficult to inspect. However, the method, according to aspects of the present invention, provides an improved method for inspecting the ring gear in a gearbox.

Figure 5:
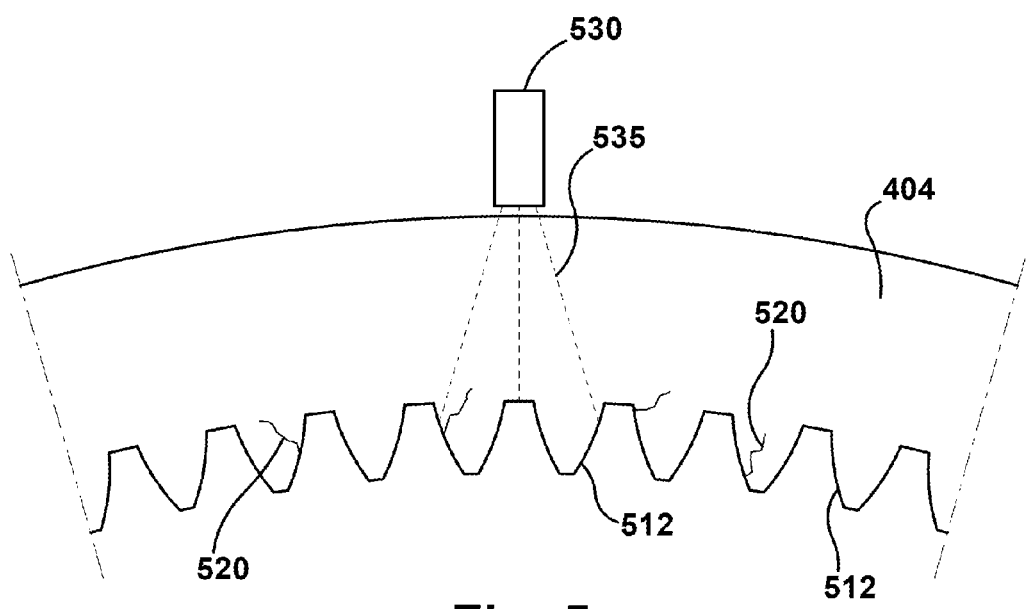
FIG. 5 is a partial, cross-sectional illustration of a ring gear shown undergoing an inspection procedure, according to an aspect of the present invention.

FIG. 5 illustrates a partial, cross-sectional view of the ring gear 404. Defects 520, such as cracks or fissures, can occur in the ring gear 404 or the ring gear teeth 512.

The ultrasonic transducer 530, according to one aspect of the present invention, can be scanned on the outside diameter of the ring gear. The wave packets propagate through the ring gear material. If defects are present in the ring gear, such as cracks 520, the sound will reflect from the cracks 520. The reflected sound waves propagating from the defects will either follow a direct path back to the transducer or propagate to a surface of the ring gear where they will reflect and propagate towards the transducer. The transducer 530 will then receive the reflected ultrasonic waves and convert the acoustic energy into electrical energy. The electrical signals will then be analyzed using ultrasonic test equipment to measure the time-of-flight for the wave reflections, the amplitude of the reflected signals, and other characteristics of the reflections such as phase, frequency, and waveform shape. This information along with the transducer beam angle and location of the transducer on the periphery of the ring gear can be used to determine the size and location of the defect or flaw in the ring gear.

An exemplary method of testing for defects in the ring gear 404 is accomplished by the appropriate selection of a signal generator, such as an ultrasonic, EMAT or a monolithic piezoelectric transducer, the appropriate positioning of the signal generator, the appropriate orientation of the signal generator, and then the activation of the signal generator.

FIG. 5 depicts an exemplary signal generator 530 for practicing the exemplary methods disclosed herein, where the dashed lines 535 represent the direction of an outgoing ultrasonic signal, to/from a region of interest (such as a crack for example) in a ring Dear tooth 512.

In view of the foregoing description, exemplary methods for testing for cracks will now be discussed. A signal generator 530 productive of a test signal 535 is selected. The signal generator 530 is positioned at an outer surface of ring gear 404. The signal generator 530 is oriented so as to direct the test signal 535, to propagate through the ring gear 404 and towards ring gear teeth 512. Once oriented, the signal generator 530 is activated so as to test the ring gear 404, which includes the ring gear teeth 512. To assure a thorough inspection of the ring gear, the signal generator 530 may be moved circumferentially and/or axially to achieve full coverage across the outer surface of the ring gear 404. Alternatively, the signal generator 530 may be moved across outer surface of ring gear 404 in any suitable pattern.

In addition to the ring gear of the gearbox, there are other ring gears or gears in general that may be inspected with the method according to the present invention. In wind turbines, the yaw gear and pitch gear also contain ring gears that could benefit from the inspection method according to the present invention. The method of inspection was described in relation to wind turbine components; however, the inspection method could be applied to any component in any machine or device having ring-type gearing.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Furthermore, the use of the terms a, an, etc. do not denote a limitation of quantity, but rather denote the presence of at least one of the referenced item.

What is claimed is:

1. A method for ultrasonically inspecting a ring gear of a gearbox for the detection, characterization and/or sizing of defects therein, the ring gear having a plurality of teeth extending radially inward with respect to an outer surface of said gearbox, the method comprising:

selecting an ultrasonic transducer productive of a test signal;

positioning the ultrasonic transducer at an outer surface of said ring gear, the ring gear located within a needle a nacelle of a wind turbine;

orienting the ultrasonic transducer so as to direct the test signal to propagate through the ring gear;

activating the ultrasonic transducer so as to test the ring gear for defects therein;

moving the ultrasonic transducer around a periphery or outer surface of the ring gear to obtain an inspection of at least a portion of the ring gear inside the gearbox while the ring gear is located within the nacelle of the wind turbine; and scanning with the ultrasonic transducer in at least one of zero-degree beam angle and multiple beam angles.

2. The method of claim 1, further comprising:
selecting an ultrasonic transducer capable of a pulse-echo mode of testing.

3. The method of claim 1, wherein the selecting an ultrasonic transducer step further comprises choosing the ultrasonic transducer from one or more of:
a monolithic transducer and a phased-array transducer.

4. A method for inspecting a component of a wind turbine for the detection, characterization and/or sizing of defects therein, the component having a plurality of teeth extending radially inward with respect to an outer surface of said component, the method comprising:
choosing the component to be tested from at least one of, a ring gear, a pitch drive gear and a yaw drive gear;
selecting a transducer productive of a test signal;
positioning the transducer at an outer surface of said component, the component located within a wind turbine;
orienting the transducer so as to direct the test signal to propagate through at least a portion of the component;
activating the transducer so as to test the component for defects therein; and
moving the transducer around the periphery or outer surface of the component, to obtain an inspection of at least a portion of said component.

5. The method of claim 4, wherein said selecting a transducer further comprises choosing a transducer of at least of the following types:

ultrasonic, electromagnetic acoustic and monolithic piezoelectric.

6. The method of claim 5, further comprising:
selecting a transducer capable of at least one of, pitch-catch mode of testing and pulse-echo mode of testing.

7. The method of claim 5, wherein the selecting a transducer step further comprises choosing the transducer from one or more of:
a monolithic transducer and a phased-array transducer.

8. The method of claim 4, further comprising:
scanning with said transducer in at least one of, zero-degree beam angle and multiple beam angles.

9. A system for inspecting a component of a wind turbine for the detection, characterization and/or sizing of defects therein, the component having a plurality of teeth extending radially inward with respect to an outer surface of said component, the system comprising:
a transducer productive of a test signal;
wherein the component is at least one of a ring gear, yaw drive component and pitch drive component; and
wherein the transducer is positioned at an outer surface of said component while the component is located within the wind turbine, and oriented so as to direct the test signal to propagate through at least a portion of the component, and wherein the transducer is employed to test the component for defects therein.

10. The system of claim 9, wherein the transducer is at least one of the following types:
ultrasonic, electromagnetic acoustic and piezoelectric.

11. The system of claim 10, wherein the transducer is capable of scanning in at least one of, zero-degree beam angle and multiple beam angles.

12. The system of claim 10, further comprising a visual display device for receiving and displaying the test signal, wherein the visual display device is used for analyzing inspection results to determine at least one of the characteristics, location and size of a defect in said component.

13. The system of claim 9, wherein the transducer is capable of at least one of, pitch-catch mode testing and pulse-echo mode testing.

14. The system of claim 13, wherein the transducer is at least one of the following types:
a monolithic transducer and a phased-array transducer.

* * * * *

UNITED STATES PATENT AND TRADEMARK OFFICE
CERTIFICATE OF CORRECTION

PATENT NO. : 8,181,528 B2  
APPLICATION NO. : 12/394160  
DATED : May 22, 2012  
INVENTOR(S) : Francis A. Reed et al.

Page 1 of 1

It is certified that error appears in the above-identified patent and that said Letters Patent is hereby corrected as shown below:

Claims
In column 7 line 4, claim 1, delete "a needle".

Signed and Sealed this
First Day of March, 2016

Michelle K. Lee
*Director of the United States Patent and Trademark Office*